(12) United States Patent
Larson (10) Patent No.: US 7,475,050 B2
(45) Date of Patent: Jan. 6, 2009

(54) SYSTEMS FOR DEVELOPING ANALYTICAL DEVICE METHODS

(75) Inventor: Paul A. Larson, Loveland, CO (US)

(73) Assignee: Agilent Technologies, Inc., Santa Clara, CA (US)

(*) Notice: Subject to any disclaimer, the term of this patent is extended or adjusted under 35 U.S.C. 154(b) by 594 days.

(21) Appl. No.: 11/144,199

(22) Filed: Jun. 2, 2005

(65) Prior Publication Data

US 2006/0273010 A1   Dec. 7, 2006

(51) Int. Cl.
*G06F 17/00* (2006.01)
(52) U.S. Cl. .............................. 706/47; 706/46; 702/12; 702/19; 210/656
(58) Field of Classification Search ............. 706/45–48, 706/50, 60, 61; 702/19, 22–32; 364/496; 210/656
See application file for complete search history.

(56) References Cited

U.S. PATENT DOCUMENTS

| | | | | |
|---|---|---|---|---|
| 5,827,946 A | * | 10/1998 | Klee et al. ................. 73/23.36 |
| 5,905,192 A | * | 5/1999 | Wikfors et al. ............. 73/23.35 |
| 5,958,246 A | * | 9/1999 | Tipler et al. ................. 210/656 |
| 6,093,327 A | * | 7/2000 | Anderson et al. ........... 210/660 |
| 6,434,490 B1 | * | 8/2002 | Agrafiotis et al. ............. 702/27 |
| 6,493,639 B1 | * | 12/2002 | Klee et al. ..................... 702/22 |
| 6,691,053 B2 | * | 2/2004 | Quimby et al. ............... 702/89 |
| 7,269,517 B2 | * | 9/2007 | Bondarenko ................. 702/19 |
| 2001/0032210 A1 | * | 10/2001 | Frank et al. .............. 707/104.1 |
| 2004/0259111 A1 | * | 12/2004 | Marlowe et al. ............... 435/6 |
| 2005/0044110 A1 | * | 2/2005 | Herzenberg et al. ...... 707/104.1 |

OTHER PUBLICATIONS

Agilent Chemstation, "Understanding Your ChemStation," Agilent Technologies Deutschland GmbH 2003.
Agilent Chemstation, "Understanding Your ChemStation," Agilent Technologies 2004.

* cited by examiner

*Primary Examiner*—David R Vincent
*Assistant Examiner*—Omar F Fernandez Rivas (57) ABSTRACT

Systems and processes for using the same for developing analytical device methods are provided. Also provided are computer program products for executing the subject processes.

10 Claims, 11 Drawing Sheets

| | Partition Information | Detection Information | Sample Source Information | Report Information |
|---|---|---|---|---|
| Instrument | Oven temperature profile<br><br>Carrier Gas flow profile | Detector Setpoints | Injection volume<br><br>Injection source | |
| Data Analysis | Retention Times | Response Factors | Calibration Amounts | Physical Constants<br>Report template<br>Custom Calculation<br>Peak Grouping<br>Pattern Recognition<br>Integration |

Table 1

SYSTEMS FOR DEVELOPING ANALYTICAL DEVICE METHODS

BACKGROUND OF THE INVENTION

Analytical chemistry is the analysis of samples to gain an understanding of their chemical composition. The goal of many chemical analysis protocols is to analyze a given sample (e.g., a physiological sample, an environmental sample, a manufacturing sample, etc.) for a variety of different purposes, such as to identify the presence of one or more analytes of interest in the sample, to characterize the makeup of the sample, for example in quality control, etc.

Many different analytical chemistry protocols have been developed. One broad category of analytical protocols that have been developed is chromatography. Chromatography is a family of analytical chemistry techniques for the separation of mixtures. In chromatography, a sample (the analyte) in a "mobile phase", often in a stream of solvent, is passed through a "stationary phase", where the stationary phase is some form of material that will provide resistance between the components of the sample and the material. Usually, each component has a characteristic separation rate that can be used to identify it and thus the composition of the original mixture.

A chromatograph takes a chemical mixture carried by liquid or gas and separates it into its component parts as a result of differential distributions of the solutes as they flow around or over a stationary liquid or solid phase. Various techniques for the separation of complex mixtures rely on the differential affinities of substances for a gas or liquid mobile medium and for a stationary adsorbing medium through which they pass; such as paper, gelatin, or magnesium silicate gel.

Many different chromatographic analytical devices have been developed in order to perform various chromatographic protocols. Examples of various chromatographic devices include, but are not limited to: gas chromatography devices, liquid chromatography devices, capillary electrophoresis devices, and supercritical fluid chromatography devices.

Chromatographic devices are typically operated according to an analytical device method, which method is used by a chromatographic device data system (e.g., such as the ChemStation system from Agilent Technologies, Palo Alto, Calif.) to provide all of the setpoints for a device to perform a given sample analysis. As such, an analytical device method generally at least includes instrument control, sample injection and data analysis setpoints. Traditionally, all of the instrument control setpoints for a given method are provided together as a package to a user, e.g., as may be provided in a plurality of selectable complete methods packaged with an analytical device, or as may be imported into the operating data system of a device as a complete method obtained from an outside source. In certain instances, it is possible to import the sample injection and/or data analysis set points as a group into a given data analysis system. In addition, certain chromatographic analytical device data systems provide for editing of one or more parameters of a pre-existing method. However, the inventors are not aware of any product that provides for the ability to selectively import instrument control information into a system that can be used by the system develop a method de novo. Prior solutions have required that the information needed to develop an analysis must be imported in the format defined for that system. For example, current versions of the Agilent ChemStation requires a pre-existing method be imported into the ChemStation methods directory.

The access to scientific information has been changed dramatically by the presence of the Internet and by advances in storage media for computers. This improved access has provided electronic access to scientific knowledge in an unprecedented fashion.

There is a need in the art to provide for the ability to capitalize on the enhanced access to scientific knowledge in the development of analytical device methods. The present invention satisfies this need.

SUMMARY OF THE INVENTION

Systems and processes for developing analytical device methods are provided. A feature of the subject systems is the presence of a method developer module, which module allows a user to enter at least one analytical device method parameter (such as an instrument control parameter) into the system, where the method developer module automatically develops a complete analytical device method based on the input parameter(s). A feature of embodiments of the invention is that the method developer module allows for the collective transfer of a plurality of parameters from a source document. A feature of other embodiments of the invention is the use by the module of one or more decision rules in developing the method. In certain representative embodiments, the interface also provides for improved integration of additional applications. Also provided are computer program products for executing the subject methods.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

By "remote location," it is meant a location other than the location at which a referenced item is present, e.g., a location outside of the application of interest (such as a package of a consumable, where the consumable may be in the same room as the application being operated, e.g., a data system on an analytical device) or another physical location, as well as for example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart.

"Communicating" information references transmitting the data representing that information as signals (e.g., electrical, optical, radio signals, etc.) over a suitable communication channel (e.g., a private or public network).

"Forwarding" an item refers to any means of getting that item from one location to the next, whether by physically transporting that item or otherwise (where that is possible) and includes, at least in the case of data, physically transporting a medium carrying the data or communicating the data.

The terms "system" and "computer-based system" refer to the hardware means, software means, and data storage means used to practice aspects of the present invention. The minimum hardware of the computer-based systems of the present invention comprises a central processing unit (CPU), input means, output means, and data storage means. A skilled artisan can readily appreciate that many computer-based systems are available which are suitable for use in the present invention. The data storage means may comprise any manufacture comprising a recording of the present information as described above, or a memory access means that can access such a manufacture.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

A "memory" or "memory unit" refers to any device that can store information for subsequent retrieval by a processor, and may include magnetic or optical devices (such as a hard disk, floppy disk, CD, or DVD), or solid-state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

In certain embodiments, a system includes hardware components which take the form of one or more platforms, e.g., in the form of servers, such that any functional elements of the system, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any convenient type of computer platform, e.g., such as a server, main-frame computer, a work station, etc. Where more than one platform is present, the platforms may be connected via any convenient type of connection, e.g., cabling or other communication system including wireless systems, either networked or otherwise. Where more than one platform is present, the platforms may be co-located or they may be physically separated. Various operating systems may be employed on any of the computer platforms, where representative operating systems include Windows, Sun Solaris, Linux, OS/400, Compaq Tru64 Unix, SGI IRIX, Siemens Reliant Unix, and others. The functional elements of system may also be implemented in accordance with a variety of software facilitators and platforms, as is known in the art.

DETAILED DESCRIPTION OF THE INVENTION

Systems and processes for developing analytical device methods are provided. A feature of the subject systems is the presence of a method developer module, which module allows a user to enter at least one analytical device method parameter (such as an instrument control parameter) into the system, where the method developer module automatically develops a complete analytical device method based on the input parameter(s). A feature of embodiments of the invention is that the method developer module allows for the collective transfer of a plurality of parameters from a source document. A feature of other embodiments of the invention is the use by the module of one or more decision rules in developing the method. In certain representative embodiments, the interface also provides for improved integration of additional applications. Also provided are computer program products for executing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the subject invention provides systems and processes for use in developing analytical device methods. Specifically, aspects of the invention provide systems and processes for automatically developing analytical device methods from one or more user input analytical device method parameters input by a user. The term "analytical device" is used broadly to refer to any type of device that performs an analysis of a sample. In representative embodiments, the analytic device is an analytical chemistry device, which is a device that analyzes samples to gain an understanding of their chemical composition. Of interest in certain embodiments are chromatographic devices, including both liquid and gas chromatographic devices. Of interest are the following representative analytical systems: Agilent Technologies GC or GC/MS systems, including 6890N GC, 5973 Inert MSD, 5973N GC/MS, 6850 Series II Network GC and 6850 Series Network GC, 3000 Micro GC, 6820 GC, etc.

The analytical devices for which the subject invention develops methods are, in representative embodiments, devices run by a data system, which data system uses setpoints provided by a given method to operate an analytical device to perform a given sample analysis. By "analytical device method" is meant all of the setpoints required by a data system to operate an analytical device or collection of analytical devices to perform a given sample analysis. In representative embodiments, an analytical device method produced by the subject processes includes instrument control, sample injection and data analysis setpoints.

Figure 1:
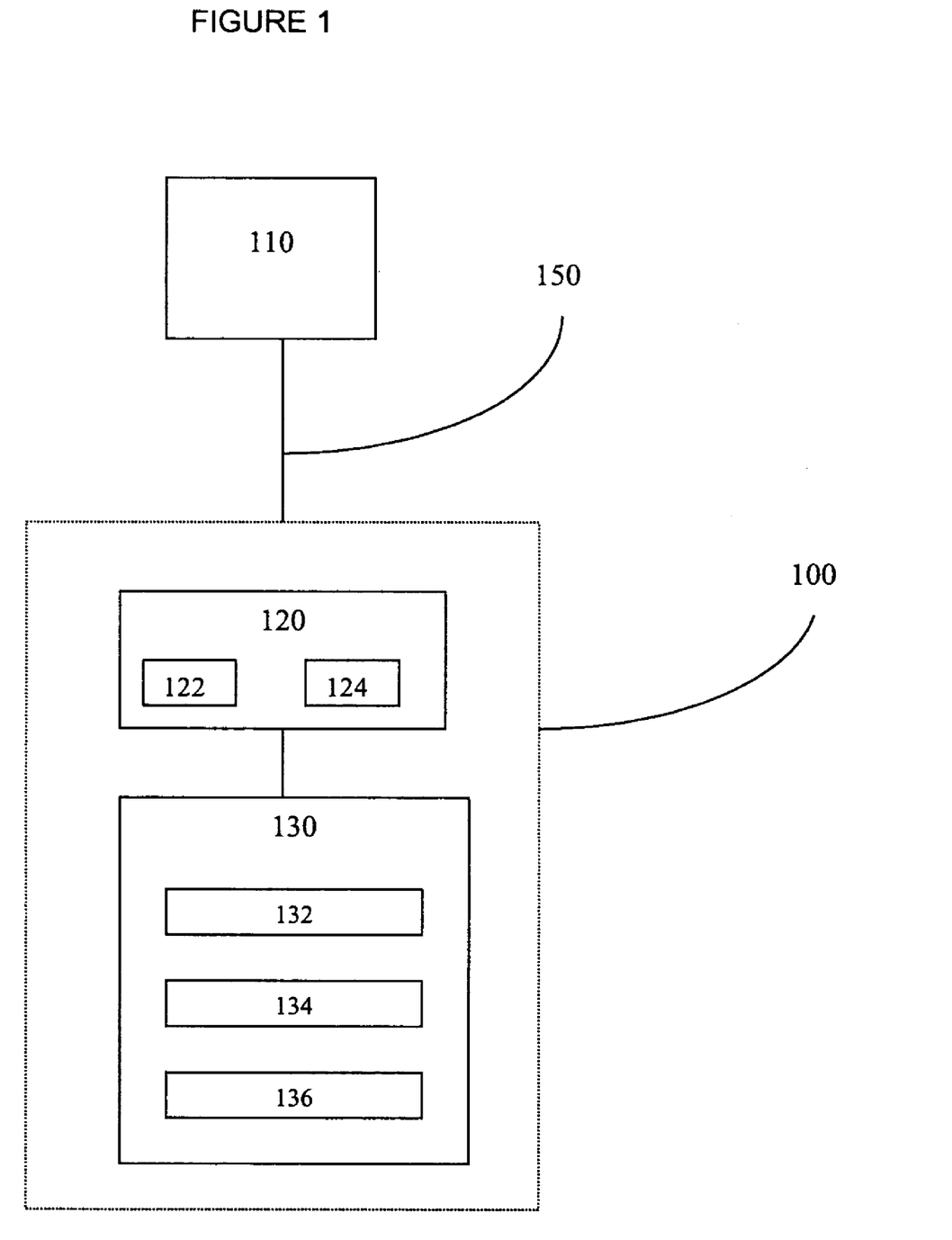
FIG. 1 schematically illustrates a system of a representative embodiment of the subject invention.

FIG. 1 provides a view of a representative system according to an embodiment of the subject invention. In FIG. 1, system 100 includes communications module 120 and processing module 130, where each module may be present on the same or different platforms, e.g., servers, as is known in the art. The communications module includes an input manager 122 and output manager 124 functional elements.

Input manager 122 receives information, e.g., parameter information, from a user e.g., locally or from a remote location (such as over the Internet or optical scanner). Input manager 122 processes and forwards this information to the processing module 130. Output manager 124 provides information assembled by processing module 130, e.g., a completed analytical device method, to a user. The communications module 120 may be operatively connected to a user computer 110 by communications means 150, which provides a vehicle for a user to interact with the system 100. User computer 110, shown in FIG. 1, may be a computing device specially designed and configured to support and execute any of a multitude of different applications. Computer 110 also may be any of a variety of types of general-purpose computers such as a personal computer, network server, workstation, or other computer platform now or later developed.

As reviewed above, the systems include various functional elements that carry out specific tasks on the platforms in response to information introduced into the system by one or more users. In FIG. 1, elements 132, 134 and 136 represent three different functional elements of processing module 130. At least one of the functional elements 132 of processing module 130 is a method developer module, and is conveniently referred to herein as the method developer module functional element of the system.

As summarized above, a feature of the subject systems is that a method developer module is employed to automatically develop an analytical device method de novo. As the methods are developed de novo, the system is distinguished from other systems in which a given method that has already been developed is merely edited by changing one or more parameters in the already complete method. Instead, the subject systems are characterized by using one or more user input analytical device method parameters to produce new analytical device methods, e.g., by applying a one or more decision rules to the user input parameters. A feature of embodiments of the invention is that the method developer module allows for the collective transfer of a plurality of parameters from a source document into the method developer module, as described in greater detail below. A feature of other embodiments of the invention is the use by the module of one or more decision rules in developing the method following input of one or more parameters. In certain embodiments, the method developer module includes both of these features.

Figure 2:
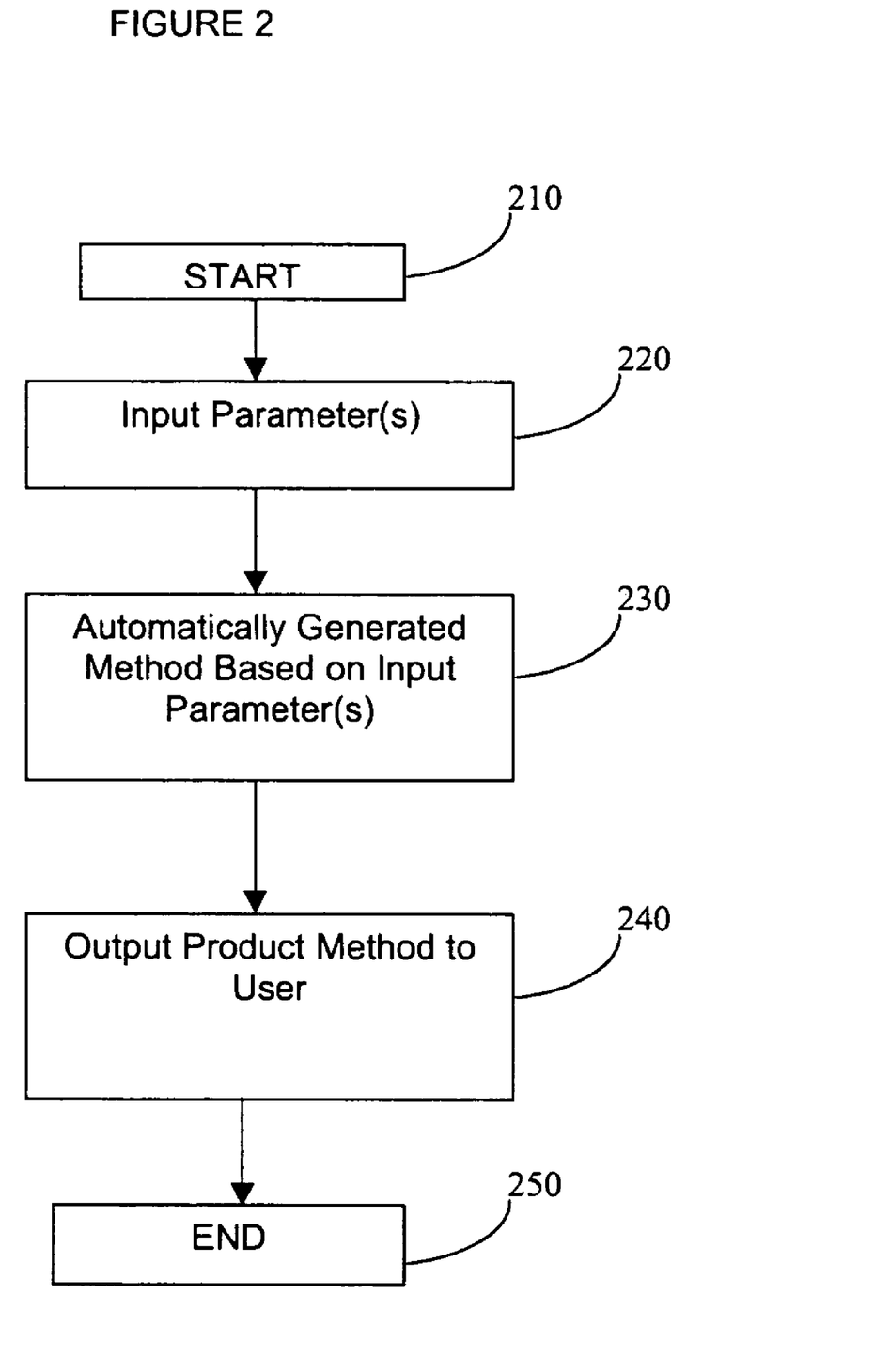
FIG. 2 provides a flow chart diagram of a first embodiment of the process used by a method developer module of FIG. 1 to generate a method.

A representative method developer module provides for method development according to the process illustrated in FIG. 2. In practicing the subject invention, a method developer module starts development at step 210 of a method by allowing a user (e.g., a researcher that is developing a method for an analytical device method) to enter at least one analytical device method parameter into the method developer module, e.g., via an interface element, such as a graphical user interface (GUI), as represented by step 220. By analytical device method parameter is meant a setpoint (or information used to determine a setpoint) that can be combined with additional setpoints to make up a complete analytical device method, where these additional setpoints may be provided by the method developer module (e.g., from a memory) or input by the user.

The input method parameter can be categorized according to the subpart or division of the overall method of which it is a member. For example, where a given method includes instrument control, sample injection, detector and data analysis subsets of setpoints, the parameter may be an instrument control parameter, a sample injection parameter, or a data analysis parameter.

By instrument control parameter is meant information that runs the device during a given sample analysis. Where the analytical device method is a method for running a gas chromatographic analytical device, examples of instrument control parameters or information include, but are not limited to: oven temperature profiles, carrier gas flow profiles, detector setpoints, etc. By sample injection parameter is meant information about sample injection for a given method, such as: injection volume, sample washes, equilibration time, load time, inject time, and the like. By data analysis profile is meant information about how obtained data is analyzed by the system and presented by the system to the user, where for gas chromatographic analytical device, representative data analysis parameters or information include, but are not limited to: retention times, response factors, calibration amounts, physical constants, report templates, custom calculations, peak grouping, pattern recognition, integration, etc.

At step 220, the user inputs one or more method parameters into information receipt fields of an interface of the method developer module. In certain embodiments, the method developer modules include an interface element that provides a field dedicated to the receipt of instrument control information. In certain embodiments, the interface includes an entry field that is dedicated to receipt of a parameter comprising data analysis information. In yet other embodiments, the interface includes both: (i) an instrument control entry field dedicated to receipt of a parameter comprising instrument control information; and (ii) a data analysis entry field dedicated to receipt of a parameter comprising data analysis information.

For a given type of entry field, the interface may include two or more entry fields, e.g., for accepting two or more different parameters that fall within a given category, e.g., two or more instrument control parameters, two or more data analysis parameters, etc. For example, a given interface could include at least two different instrument control entry fields and at least two different data analysis entry fields. In representative embodiments, the system includes at least an instrument control parameter dedicated entry field, where the process illustrated in FIG. 2 includes providing to the method developer module at least one instrument control method parameter at step 220.

In certain embodiments, a given interface may include a functionality (hereinafter referred to as a "knowledge agent") that enables a user to: (a) collectively select from a source location a plurality of analytical device method parameters of interest for the analytical device method that is being developed; and (b) enter the plurality of parameters as a group (i.e., collectively) into the method developer module. By source location is meant a location, or locations, at which the parameters of interest are located. In representative embodiments, the source location is an electronically accessible file or combination of files (or analogous collection of data), such as may be located at a website on the World Wide Web, a computer readable medium, etc. Examples of source locations include vendors of consumables, which vendors provide electronic publications of sample analyses, e.g., in the form of chromatograms etc., from which method parameters, e.g., instrument control parameters, may be obtained. The method developer module that includes the Knowledge Agent element may include the element as an integrated component of the method developer module or as a separate, co-existing application on the data system that includes the method developer module.

The knowledge agent, in certain embodiments, provides the user with the ability to use a selection device, such as a cursor, to select information from an outside information source, e.g., an electronic catalog provided at a vendor website, an optically scanned version of document, etc., and input the selected information into the method developer module, e.g., by dragging and dropping the selected information into the method developer module via an appropriate field of an interface. An example would be to use the cursor to draw a box around the oven and flow information of a an electronically provided chromatogram (as shown by the dashed line on the chromatogram shown in FIG. 7), where the electronically provided chromatogram may be provided at a vendor website or in a published article, or scanned locally by an optical scanner device, where selection may include a right click to copy, followed by a drag and drop step to place the selected information into an appropriate field of an interface, e.g., a method acquisition tab of the interface of to the system. The method developer module of the system would then use the input information for development of the method.

Figure 7:
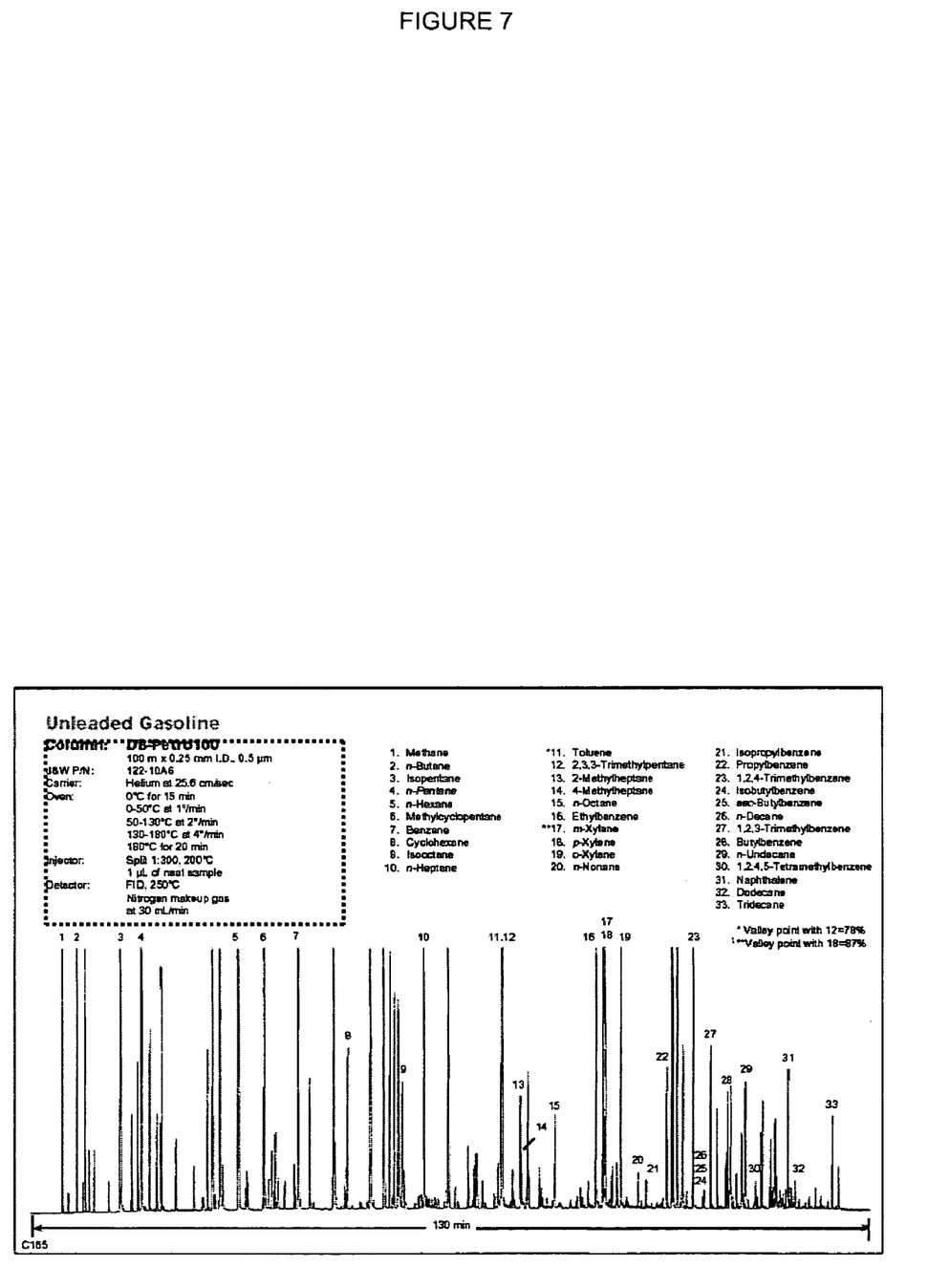
FIG. 7 provides a sample chromatogram, a portion of which may be selected by a knowledge agent embodiment of an embodiment of the invention.

A feature of certain embodiments is that the knowledge agent allows a user to select only a portion of the total data that is present at the source location, i.e., only a first subset of the total data present at the source location. The first subset may be made up of qualitative and/or quantitative data. For example, source location may be a chromatogram that includes the instrument operating protocols used to generate the chromatogram, e.g., as illustrated in FIG. 7. Using the knowledge agent, only the operating parameters may be collectively chosen from a chromatogram as shown in FIG. 7, e.g. by using a selection tool to selectively choose only these parameters, as shown by the information within the dashed square on the chromatogram. The selected parameters may then be copied and input into the method developer module. Selection may be accomplished using any convenient format. In certain embodiments, one may employ a selecting device, e.g., a mouse, to point and click on the data of interest.

Following input of the one or more method parameters at step 220, the method developer module automatically generates an analytical device method at step 230. In automatically generating the analytical device method, the method developer module may execute one or more decision trees, e.g., to automatically determine a setpoint or collection of setpoints based on an input parameter. For example, in certain embodiments, following input of one or more parameters, the method developer module at step 230 determines the injector and detector set-points through a predetermined set of one or more decision rules. As an example, the method developer module may determine the detector temperature by the following representative decision rule:

The detector temperature for a given detector is the greater of the three choices

250° C.

20° C.+the final oven temperature

20° C.+the postrun temperature

In another representative example, the method developer module at step 230 may also determine the detector flow rates according to the following representative decision rule:

30 ml/min Hydrogen;

400 ml/min Air; and 25 ml/min=Column flow+Makeup Gas Flow.

The injection port in these representative embodiments has a similar set of decision rules for determining the injection port set points, e.g., based on the partition part of the method, the type of sample input device and possible regulatory requirements (e.g., methods performed in accordance with Environmental Protection Agency (EPA) requirements). The method developer module may employ different decision rules at step 230 for different detectors for "automatically" setting up methods.

In certain embodiments, once the method is generated at step 230, the generated method is output at step 240 to the user. In the embodiment shown in FIG. 2, this represents the end 250 of the process performed by the method developer module.

Figure 3:
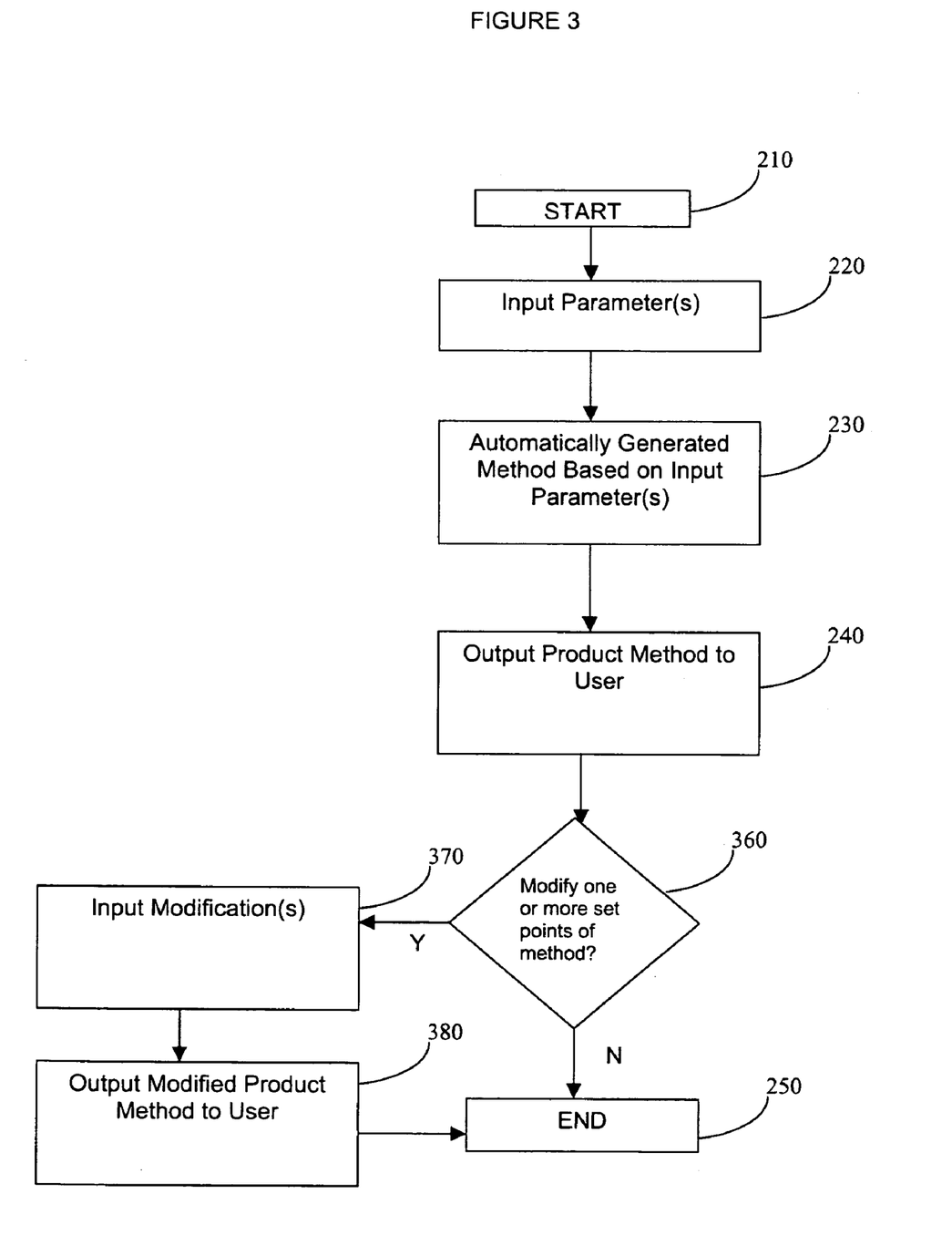
FIG. 3 provides a flow chart diagram of a second embodiment of the process used by a method developer module of FIG. 1 to generate a method.

In certain embodiments, one or more of the setpoints of the product method 240 can be modified further, e.g., as illustrated in FIG. 3. The process shown in FIG. 3 is the same as that of FIG. 2, but includes additional method editing steps of 360 to 380. In the process depicted in FIG. 3, the initial output method of step 240 is reviewed to determine whether it is acceptable. If the method is acceptable as determined at step 360, the process proceeds to the end, and the initial output method is employed. If the output method is not acceptable, e.g., it is determined at step 360 that one or more method modifications should be made, the system proceeds to method modification step 370, where one or more input(s) are entered to the method developer module. These inputs may be in the form of modified setpoints and or in the form of modifications to decision rules employed by the method developer module to determine setpoints based on inputs. For example, following generation of an initial method, one or more of the decision rules of the method developer module may be modified at step 360. Modification of the decision rules may include modification of threshold values, and/or modification of underlying logic rules, as desired. For example, where a method developer module determines a detector temperature, in certain embodiments step 360 allows a user to make changes to the threshold temperature values, but not the underlying logic, in the decision rules of the method developer module.

Figure 4:
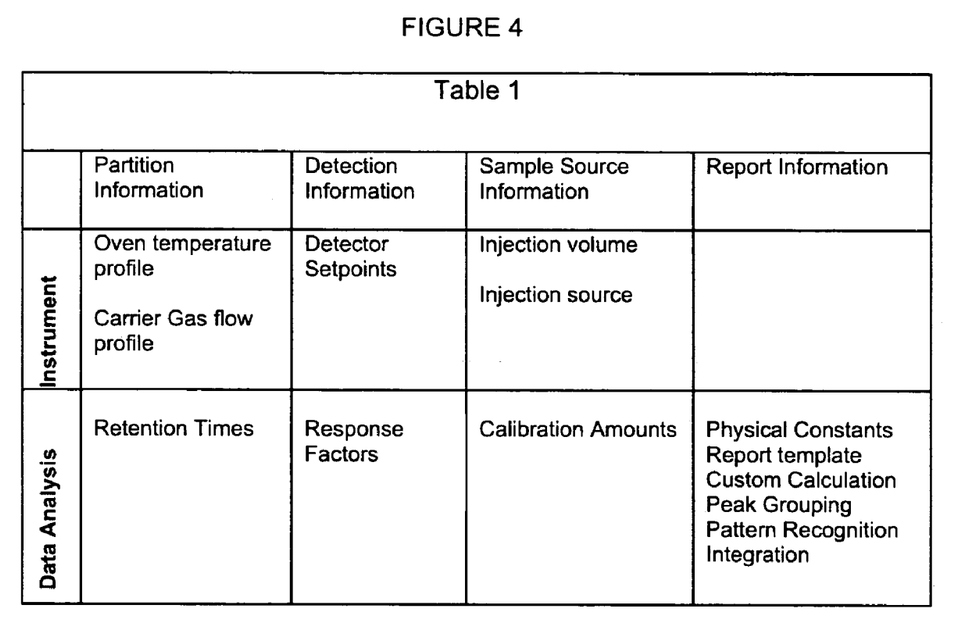
FIG. 4 provides an organization table shown how a method developer module is structured according to an embodiment of the subject invention.

The method developer module may be structured according to any convenient format that provides for the receipt of information from a user in order to develop a given method. In certain embodiments, the module is structured a format that includes two broad categories of instrument control and data analysis. Each of these broad categories may then be divided into to two or more subcategories, e.g., partition information, detection information, sample source, and report information, etc., as may be desired. An example of such a format is provided below in Table 1, shown in FIG. 4.

In using the method developer module structured according to the format of Table 1, in one representative embodiment, the user transfers instrument control parameters, e.g., the oven program and flow conditions, along with the column information, e.g., as obtained from a source document, such as from a catalog or an on-line information source, into appropriate fields of the interface provided by the method developer module (represented as step 220 on FIGS. 2 and 3). The user can also input sample source information and detection information into appropriate fields of the interface (also represented as step 220 on FIGS. 2 and 3), where the method developer module then associates the input information with the particular instrument to be used. The method developer module then produces a complete analytical device method based on the input instrument control parameters (represented by step 230 on FIGS. 2 and 3).

In certain embodiments of the subject systems, the systems may include (e.g., as part of the interface element that provides for entry of information to a method developer module or as a separate interface element) one or more additional functionalities or applications that are desirable for a given analytical device method, e.g., as represented by modules 134 and 136 of FIG. 1. Examples of such additional functionalities include, but are not limited to: Retention Time Locking, Method Translation, Deans Switching setup, Connection to Knowledge Databases, Experimental Design, Pattern Recognition, etc. These representative additional functionalities are now described in greater detail below.

In certain embodiments, a system of the subject invention includes a Retention Time Locking (RTL) functionality, e.g., present as an integrated component of the method developer module or as a separate, co-existing application on the data system that includes the method developer module. As is known in the art, RTL is a technique that allows for variations in the columns and instruments used for the same instrument conditions (the oven temperature profile). RTL is described in U.S. Pat. No. 6,493,639, the disclosure of which is herein incorporated by reference. A given data system for an analytical device that includes RTL capability may provide for one or more of the following two abilities: (a) the ability to use a locking compound to provide a means for easy adjustment of the retention time of the locking compound to give measured retention times near the compound's retention times in the method's calibration table; and (b) the ability to compare measured retention times to the retention times in a Retention Time Table for a predetermined set of compounds, such as pesticides, FAMES, phenols, etc. RTL methods are usually based on a method that has already been optimized for a particular set of operating conditions on a particular type of column. Once the method has been optimized to give the necessary separation, the column must be calibrated. Calibration is accomplished by running an analysis a series of pressures, such as at the method's pressure (mP), mP+10%, mP+20%, mP−10%, and mP−2.0%. The results of these runs are employed to generate a second order equation describing the relationship of the locked compound's retention time to the pressure. Once this relationship is determined, the adjusted pressure can be determined to give the locked compound's retention time.

Where the subject systems provide for RTL functionality, they may provide for the import of an RTL portion of an already established method into the data system. The system may then use the imported information to generate and save an RTL calibration curve. To provide for this functionality, the system may be enabled for the automation of incrementing and decrementing the pressure of the system and making the runs automatically. With the proper choice of the sample and locking compound, the system may automatically identify the locking compound thru widening the retention time windows and/or SPID. A Retention Time-Column Pressure Calibration Curve can be generated automatically in certain embodiments. In certain embodiments, the system also enables the transfer of calibration information established for a first system into a different system with a different instrument configuration. In certain embodiments, the system enables the importation of already developed Retention Time Tables. This feature may be provided in any convenient manner, e.g., as an extra tab in a Calibration view, much like the Physical Constants Table for RGA (Residual Gas Analyzer). In certain embodiments, another method type is added to the method list of a given data system, (e.g., Standard, Refinery Gas, and RTL methods).

In certain embodiments, a system according to the invention may further include a Method Translation functionality, e.g., present as an integrated component of the method developer module or as a separate, co-existing application, e.g., on the data system that includes the method developer module. For example, a given method that has been developed from user input parameters using the method developer module as depicted in FIGS. 2 and 3 may then be translated, as desired, using a Method Translator functionality provided by the subject system.

A representative Method Translator functionality is one that provides for input of information in response to one or more queries, e.g., in the form of a Method Translator Wizard. This Method Translator functionality may be part of the process shown in FIG. 3, e.g., performed at step 370. Using the subject approach, the amount of information to be entered is significantly reduced as compared to other Method Translation protocols by making method translation a part of the method editing. For example, in certain embodiments, in response to a series of queries from the Method Translator functionality, the desired changes in column dimensions are inputted by a user, along with any desired changes in outlet and ambient pressures, and information regarding whether the carrier gas will be changed.

Figure 5:
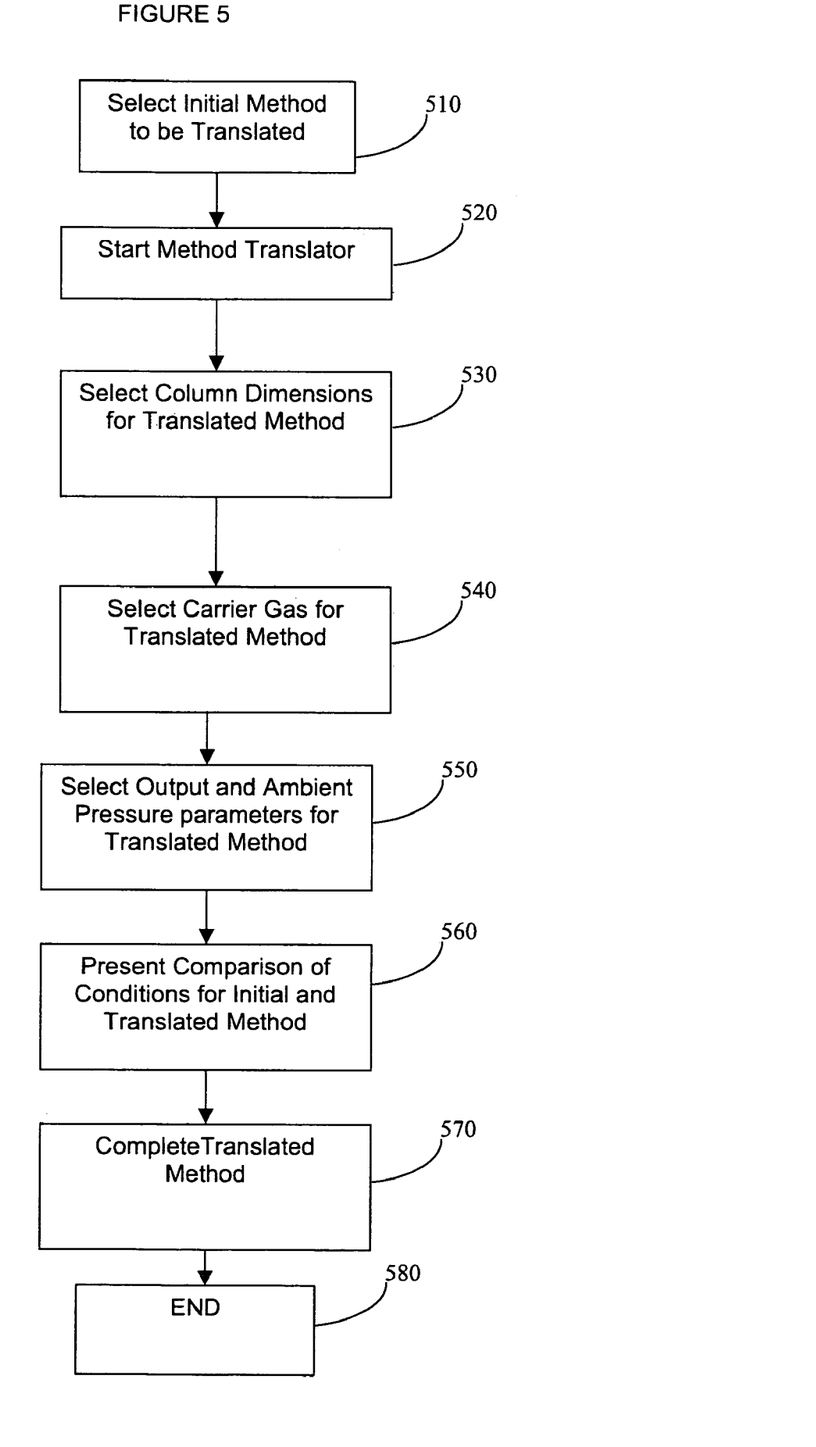
FIG. 5 provides a flow chart diagram of a process performed by a Method Translator wizard according to an embodiment of the subject invention.

A representative embodiment of a Method Translator functionality is illustrated in FIG. 5. First, at step 510 an initial method is selected, such as the method produced using the method developer module, e.g., as illustrated in FIG. 2. This method could be a calibrated method. A Translate Method task is then selected, e.g., on the interface, e.g., from a drop down menu or a by clicking on a button, as shown at step 520. Selection launches a query application, e.g., in the form of a "wizard," which presents to the user at least one input box, and sometimes a series of input boxes (i.e., fields). In the embodiment shown in FIG. 5, the first screen of the wizard asks for the column dimensions (column length, column inner diameter, and column phase thickness), which are input at step 530. Alternatively, this step may include the selection of the column from a column inventory. Next, a second screen may query the user as to whether the carrier gas will be changed, e.g., with the carrier gas selected from a drop down menu, as represented at step 540. The default would be the present carrier gas. Next, the third screen 550 presents queries for selection of the Outlet and Ambient Pressure (e.g., in the pressure units used in the method). The next screen then presents, at step 560, the comparison of the conditions for original method and the translated method. Selecting complete translation, e.g., at step 570, generates a preliminary Calibration Table based on the present calibration table retention times. (The preliminary Calibration Table values could be the original retention time values divided by the speed factor.) The completed method, as desired, may then be saved as a new method, or saved as the original method (in which case the instrument configuration of the method should be changed).

Figure 6:
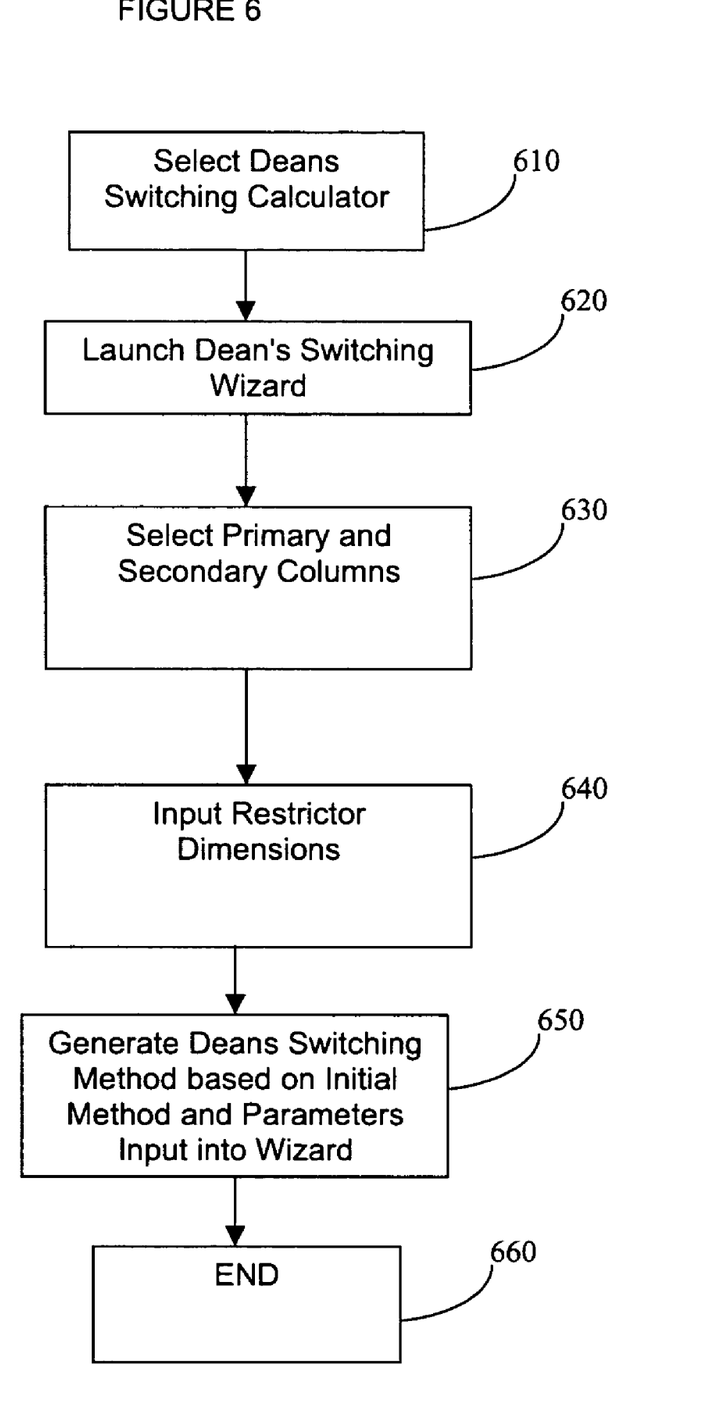
FIG. 6 provides a flow chart diagram of a process performed by a Deans Switching wizard according an embodiment of the subject invention.

In certain embodiments, a given system may include a Deans Switching setup functionality, e.g., present as an integrated component or as a separate, co-existing application. In certain embodiments, this Deans Switching setup functionality is provided as a Deans Switching calculator. As with the Method Translator functionality, the Deans Switching calculator functionality may take the form of a "wizard," as illustrated in FIG. 6. In the Deans Switching wizard illustrated in FIG 6, at step 610 a user selects the Dean Switching Calculator tab on a given interface, which launches the Deans Switching wizard at step 620. The first screen generated by the wizard at step 630 asks for identification of the primary and secondary column, e.g., by applying labels to the columns identified as column 1 and column 2 in the method. At step 640, restrictor dimensions are input. Next, at step 650 the system calculates the pressures and inputs them into the initial method to produce a method including Deans Switching. As desired, the restrictor and column configuration could be saved as part of the method. Additional macros, e.g., as currently available for the ChemStation data system, may be employed which help set up the valve times for the heart cuts. The Deans Switching Wizard as described above and illustrated in FIG. 6, could be accessed through a drop-down menu or a checklist and could be grayed out unless the instrument to be operated by the method is configured with a PCM or Aux EPC.

In certain embodiments, a given interface may include a functionality that provides for a direct link to existing knowledge bases, such as knowledge databases available from organizations such as ASTM, ISO, EPA, etc., as well as vendors of analytical devices and consumables therefore, which provide method information. In certain embodiments, the knowledge base link functionality allows the user to readily access, copy and paste this information into the method developer module. The data system that includes the knowledge base link may include the element as an integrated component of the method developer module or as a separate, co-existing application on the data system that includes the method developer module.

In certain embodiments, a given interface may include a functionality that provides for Experimental Design. The experimental design functionality allows a user to input deltas in flow and temperature setpoints to look at the sensitivity of the retention times to changes in these setpoints. In certain embodiments, this Experimental Design is provided as an adjunct to method validation, where method validation is used to prove the robustness of a particular method. The data system that includes the experimental design functionality may include the element as an integrated component of the method developer module or as a separate, co-existing application on the data system that includes the method developer module.

In certain embodiments, a given interface may include a functionality that provides for the input of Pattern Recognition parameters and/or selection of an appropriate Pattern Recognition application. The data system that includes the Pattern Recognition functionality may include the element as an integrated component of the method developer module or as a separate, co-existing application on the data system that includes the method developer module.

Figure 8A:
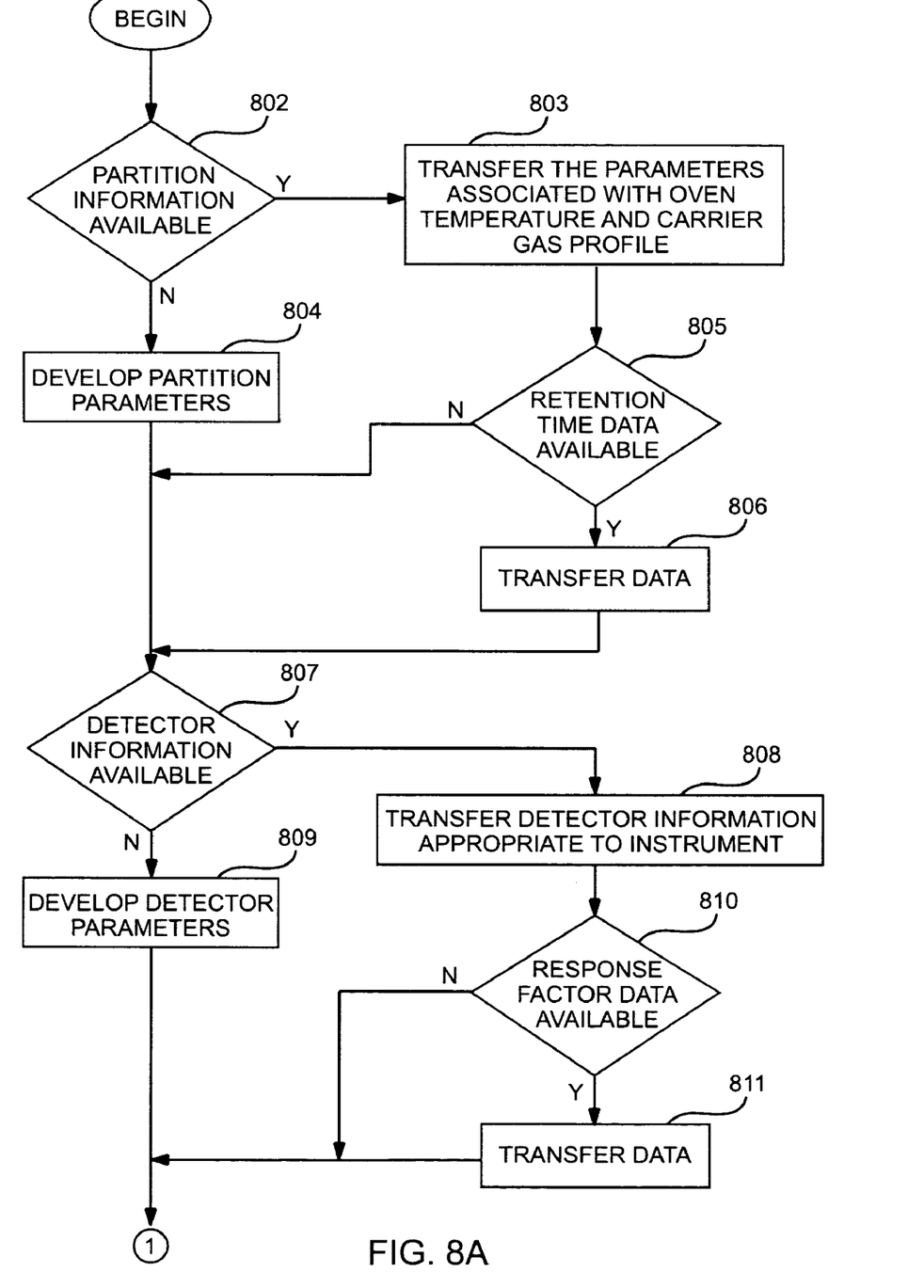
FIGS. 8A to 8D provide a flow chart diagram of a process performed by system according to an embodiment of the invention.

FIGS. 8A to 8D provide a flow chart of a process that is performed in method development according to a representative embodiment of the invention. The method developer module of FIGS. 8A to 8D is representative of embodiments of the method developer module in which the partition portion of the method is developed first, and the novel knowledge agent functionality and decision rules are employed, as reviewed above. In FIG. 8A, the system first determines at step 802 where partition information is available, e.g., from an electronic source, such as a chromatogram shown in FIG. 7. If no, the partition parameters are developed at step 804, e.g., by using a wizard protocol to query the user for relevant parameters. If yes, at step 803 the available partition information, e.g., parameters associated with the temperature and carrier gas profile, are transferred to the system collectively using the novel knowledge agent functionality of the method developer module, e.g., by selecting these parameters from the chromatogram shown in FIG. 7. At step 805, following transfer of oven temperature and carrier gas parameters to the system, the method determines whether retention time data is available. If yes, this information is transferred to the method developer at step 806, e.g., using the novel knowledge agent functionality.

Next, at step 807 the system determines whether detector information is available, e.g., from a source document. If no, the detector information is developed at step 809, e.g., by using a wizard protocol to query the user for relevant inputs. If yes, at step 808, the available detector information is transferred to the system, e.g., using the novel knowledge agent functionality. Following step 808, if performed, the system may then determine at step 810 whether response factor data is available. If yes, the response factor data is transferred to the system, as shown at step 811, e.g., by using the novel knowledge agent functionality.

Figure 8B:
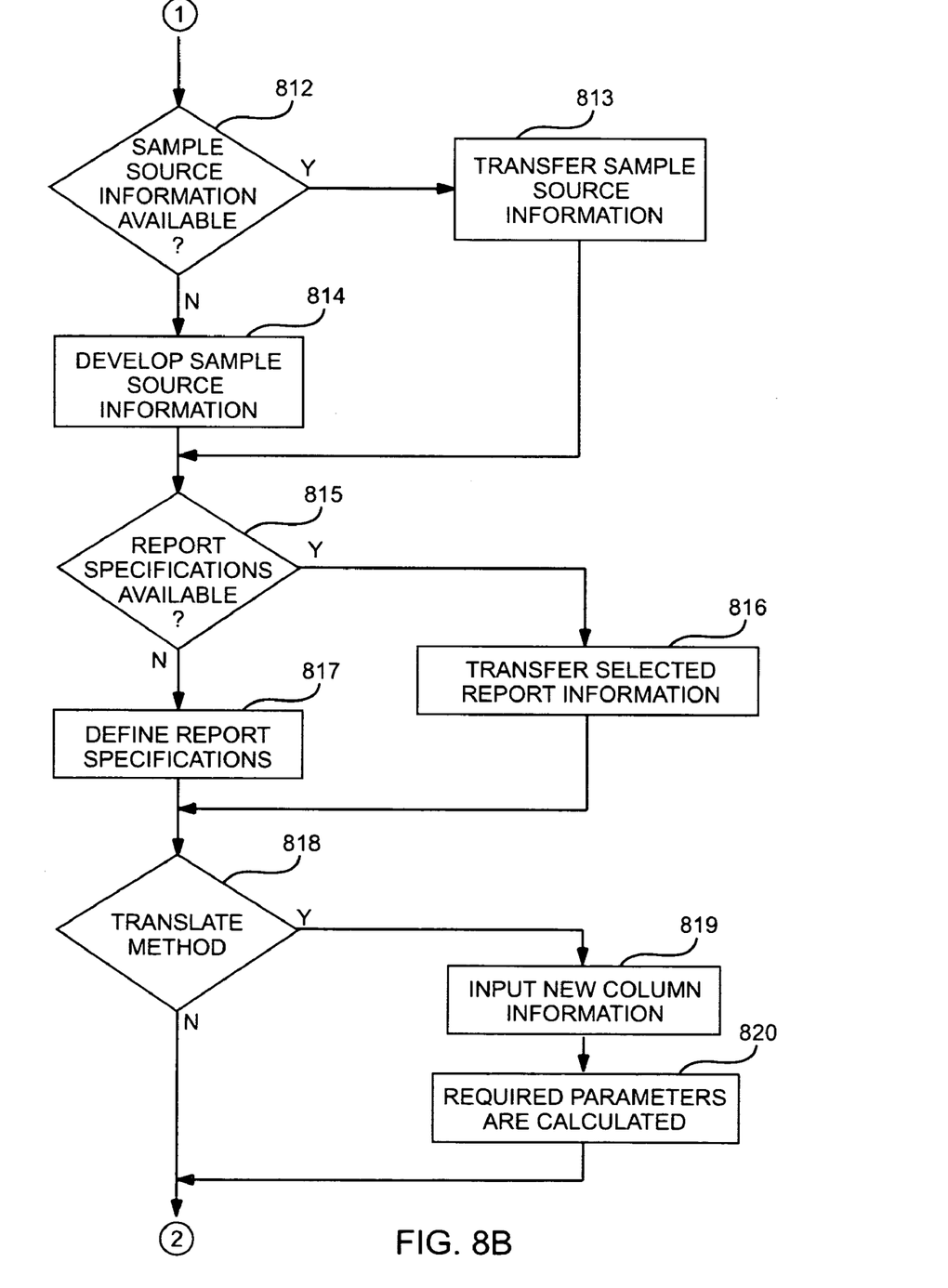

In FIG. 8b, the next step of the process performed by the system is at step 812, where a determination is made as to whether sample source information is available, e.g., from a source location. If no, sample source information is developed at step 814. If yes, the sample source information is transferred to the system at step 813, e.g., using the novel knowledge agent of the invention. Next, at step 815, a determination is made as to whether report specifications are available. If no, the report specifications are defined at step 817. If yes, selected report information is transferred to the system at step 816, e.g., using the novel knowledge agent of the invention.

Next, at step 818 a determination is made as to whether method translation is needed. If no, the system proceeds to step 821 shown in FIG. 8C. If yes, the system requests input of new column information at step 819. Following input of the new column information at step 819, the required parameters are calculated by the system at step 820.

Figure 8C:
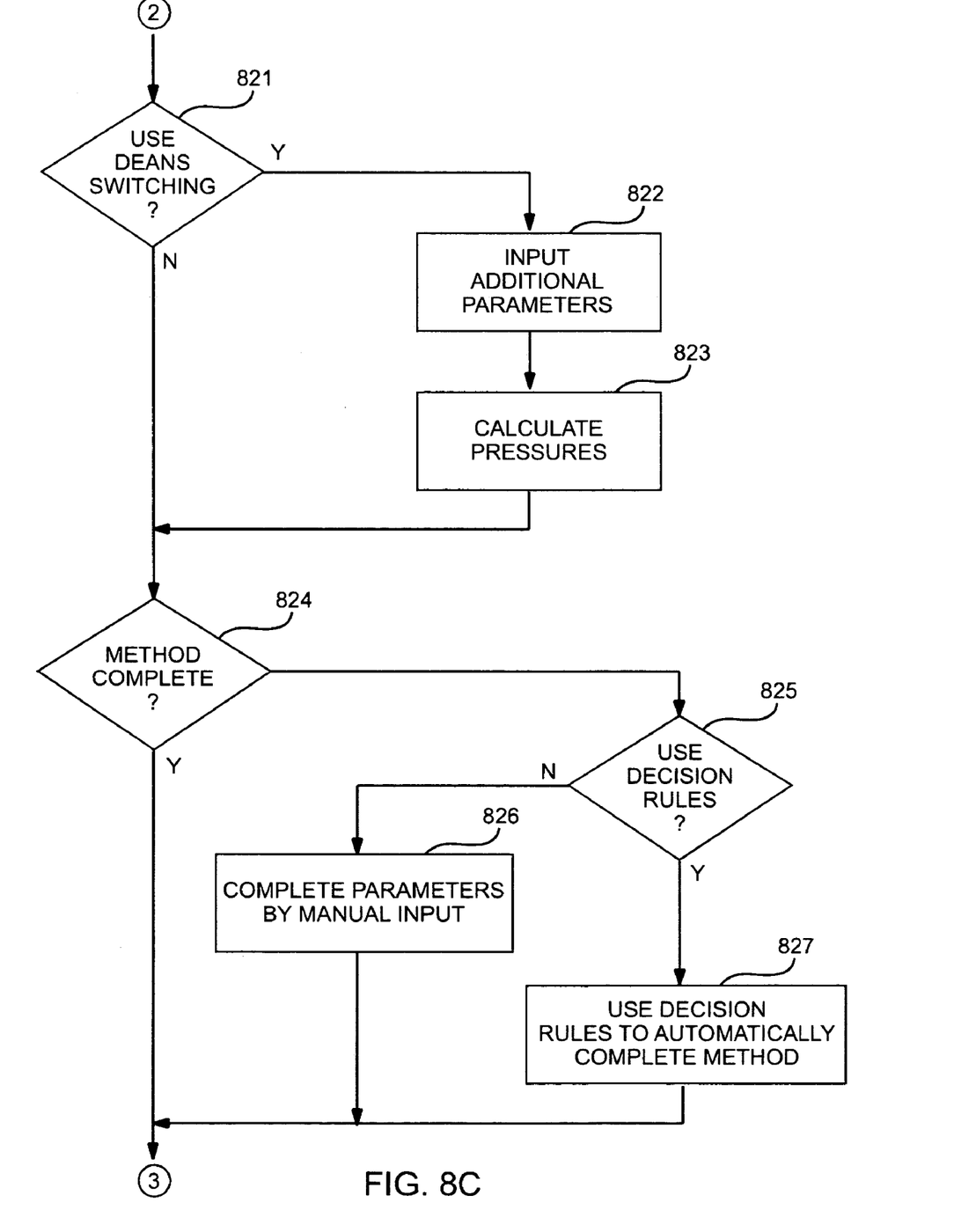

The next step of the process performed by the system is shown in FIG. 8C at step 821. At step 821, a determination is made as to whether the method being developed is to include Deans switching. If no, the system proceeds to step 824. If yes, additional parameters such as primary and secondary column information are input at step 822 and pressures are calculated at step 823.

At step 824, a determination is then made as to whether the method is complete. If yes, the system proceeds to step 828 of FIG. 8D. If no, the system proceeds to step 825, where a determination is made as to whether to employ decision rules to complete the method. If the determination at step 825 is no, any remaining parameters that needed to be determined are manually input at step 826. If the determination at step 825 is yes, decision rules are employed to automatically complete the method at step 827.

Figure 8D:
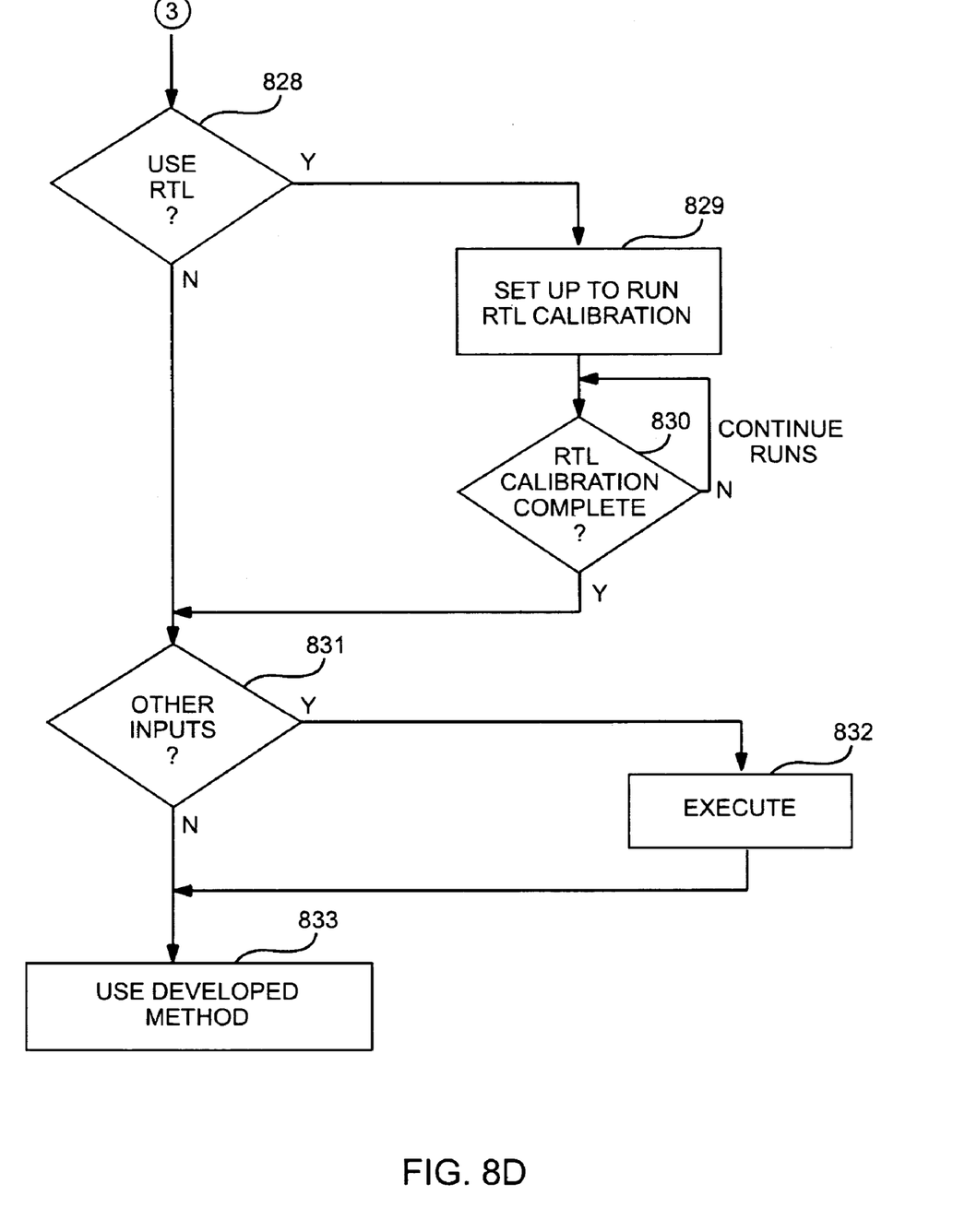

As shown in FIG. 8D, the system then determines at step 828 whether the method is going to use RTL. If no, the system proceeds to step 831. If ye, the system proceeds to step 829, where one or more RTL calibrations are run until a determination is made at step 830 that the RTL calibration is complete.

Finally, at step 831 the system determines whether any other inputs are needed. If yes, these inputs are made at step 832. If no, the resultant completed method is ready for use, as represented at step 833.

In general, the subject systems are applicable to the generation of analytical device methods for any type of analytical device. However, for ease of description only, the invention was described above in view of the representative embodiments of gas chromatography method development. It should be noted, however, that the invention is not limited to these particular representative embodiments.

The invention also provides programming, e.g., in the form of computer program products, for use in practicing the methods. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above-described methodology.

It is evident from the above description that the subject invention provides a number of advantages. Advantages include the ability to access numerous disparate sources of method relevant information in a manner that facilitates rapid and easy development of analytical device methods. As such, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A computer-implemented software system for developing an analytical device method for a chromatographic device, comprising:
 a communication module to communicate with a user via an external user interface unit:
 a processing module, further comprising:
  a method developer module, wherein the method developer module automatically develops a complete analytical device method based on an analytical device method parameter provided by the user through the external user interface unit and communicated via the communication module, wherein the method developer module automatically develops the complete analytical device method by executing at least one decision rule to determine at least one analytical device setpoint based on the user provided analytical device method parameter, wherein the complete analytical device method includes instrument control, sample injection and data analysis setpoints for the chromatographic device, wherein the user can review the complete analytical device method and, if desired, modify the complete analytical device method via the external user interface unit; and operating the chromatographic device based on the complete analytical device method developed.

2. The system according to claim 1, wherein the external user interface unit provides a user interface that includes at least one entry field for receiving entry of said parameter.

3. The system according to claim 2, wherein said user interface is a graphical user interface.

4. The system according to claim 1, wherein said system comprises a Knowledge Agent element that enables a user to: (a) collectively select a plurality of analytical device method parameters of interest from a source location for said analytical device method; and (b) enter said plurality of parameters as a group into said system for use in developing said method.

5. The system according to claim 1, wherein said chromatographic device is a gas chromatographic device.

6. The system according to claim 1, wherein said system further includes a Retention Time Locking functionality that provides for entry of Retention Time Locking parameters into said system for use in developing said method.

7. The system according to claim 1, wherein said system further includes a Method Translator element that provides for entry of Method Translation information into said system for use in developing said method.

8. The system according to claim 1, wherein said system further includes a Deans Switching element that provides for entry of Deans Switching information into said system for use in developing said method.

9. The system according to claim 1, wherein said system further includes an Experimental Design element that provides for entry of experimental design information into said system for use in developing said method.

10. The system according to claim 1, wherein said system further includes a Pattern Recognition element that provides for entry of Pattern Recognition information into said system for use in developing said method.

* * * * *